US00RE44206E

(19) United States
(12) Reissued Patent
Ferguson et al.

(10) Patent Number: US RE44,206 E
(45) Date of Reissued Patent: May 7, 2013

(54) OXIDATION PROCESS FOR THE PRODUCTION OF CARBOXYLIC ACIDS AND ALKENES

(75) Inventors: Ewen James Ferguson, Beverley (GB); Andrew Richard Lucy, Brough (GB); Mark Stephen Roberts, Beverley (GB); Diana Rachel Taylor, Brough (GB); Bruce Leo Williams, Brough (GB)

(73) Assignee: BP Chemicals Limited, Middlesex (GB)

(21) Appl. No.: 13/067,186

(22) Filed: May 16, 2011

Related U.S. Patent Documents

Reissue of:
(64) Patent No.: 7,262,322
Issued: Aug. 28, 2007
Appl. No.: 10/557,191
Filed: Nov. 17, 2005

(30) Foreign Application Priority Data

Jun. 5, 2003 (GB) ..... 0312965.7

(51) Int. Cl.
*C07C 67/00* (2006.01)
*C07C 51/16* (2006.01)

(52) U.S. Cl.
USPC ..... 560/241; 562/544; 562/549

(58) Field of Classification Search ..... None
See application file for complete search history.

(56) References Cited

U.S. PATENT DOCUMENTS

| | | | |
|---|---|---|---|
| 6,040,474 | A | 3/2000 | Jobson et al. |
| 6,143,921 | A | 11/2000 | Karim et al. |
| 6,156,928 | A | 12/2000 | Karim et al. |
| 6,180,821 | B1 | 1/2001 | Jobson et al. |
| 6,670,504 | B1 | 12/2003 | Borchert et al. |

FOREIGN PATENT DOCUMENTS

| | | | |
|---|---|---|---|
| EP | 0 495 504 | A2 | 7/1992 |
| EP | 0 926 126 | A1 | 6/1999 |
| EP | 1 201 630 | A2 | 5/2002 |
| EP | 1 201 631 | A2 | 5/2002 |
| WO | WO 01/90042 | A1 | 11/2001 |
| WO | WO 01/90043 | | 11/2001 |
| WO | WO 01/90043 | A1 | 11/2001 |

*Primary Examiner* — Paul A Zucker
(74) *Attorney, Agent, or Firm* — Nixon & Vanderhye

(57) ABSTRACT

An oxidation process for the production of alkenes and carboxylic acids from a feed comprising alkene and/or alkane, carbon monoxide, a molecular oxygen containing gas and optionally water in the presence of an oxidation catalyst in which the level of carbon monoxide is maintained between 1% and 20% by volume of the total feed to the reactor.

30 Claims, 2 Drawing Sheets

OXIDATION PROCESS FOR THE PRODUCTION OF CARBOXYLIC ACIDS AND ALKENES

Matter enclosed in heavy brackets [ ] appears in the original patent but forms no part of this reissue specification; matter printed in italics indicates the additions made by reissue.

This application is the U.S. National Phase of International Application PCT/GB04/002069, filed 13 May 2004, which designated the U.S. PCTIGB04/002069 claims priority to British Application No. 0312965.7 filed 5 Jun. 2003. The entire content of these applications are incorporated herein by reference.

The present invention relates to a process for the oxidation of a $C_2$ to $C_4$ alkane and/or alkene to produce the corresponding alkene and/or carboxylic acid and, in particular, to a process for the oxidation of ethane to ethylene and acetic acid. The present invention also relates to integrated processes in which said alkene and carboxylic acid are used as reactants for the production of alkenyl carboxylates or alkyl carboxylates.

The catalytic gas phase oxidation of ethane to ethylene and acetic acid is known. In 1978, Union Carbide Corporation published a report in the Journal of Catalysis describing a fixed bed process for the oxidation of ethane to ethylene. In addition, several U.S. Pat. Nos. (4,250,346, 4,524,236, 4,568,790, 4,899,003 and 4,596,787) describe the low temperature oxydehydrogenation of ethane to ethylene. U.S. Pat. No. 4,899,003 describes a process for the oxydehydrogenation of ethane in which the product stream comprises ethylene, acetic acid, carbon oxides and unreacted ethane. CO and $CO_2$ are removed prior to recycling the unreacted ethane. Carbon monoxide may be removed, for example, by oxidation to carbon dioxide and subsequent adsorption.

EP-A-0546677 describes a process for the oxidation of ethane to acetic acid in a fluidised bed reactor. In the process described in EP-A-0546677 most of the reactor effluent is recycled to the reactor in order to maintain a high concentration of carbon oxides as diluents in the reactor. (These diluents help to control the temperature.) However, a purge stream is taken from the reactor effluent to prevent a continual build-up of carbon oxides in the reactor. In the example of EP-A-0546677 the feed to the reactor contains 25% CO and over 40% $CO_2$. One disadvantage of high CO and $CO_2$ concentrations in the feed is that there is a reduction in the partial pressures of ethane and ethylene, which may reduce the rate of the oxidation reaction.

WO 01/90042 and WO 01/90043. both disclose an integrated process for the production of vinyl acetate, the first step of which is the oxidation of ethane to acetic acid and ethylene, with subsequent conversion of the acetic acid and ethylene to vinyl acetate. Carbon monoxide may be produced as a by-product in the conversion step to vinyl acetate. The CO may be recycled to the oxidation reactor, however, the concentration of carbon monoxide in the recycled feed is relatively low. Specifically, WO 01/90042 and WO 01/90043 disclose that usually low amounts of carbon monoxide (<100p pm) are formed in the acetic acid and ethylene production step(s), and that if carbon monoxide is produced in higher amounts (up to 5%), then a CO removal step may be required. WO 01/90042 and WO 01/90043 do not disclose any benefits of maintaining an amount of CO in the feed to the reactor.

EP-A-0 877 727 discloses an integrated process for the production of acetic acid and/or vinyl acetate in any predetermined and variable proportions from a gaseous feedstock comprising ethylene and/or ethane. The integrated process comprises a first step wherein ethylene and/or ethane is catalytically oxidised in a first reaction zone to produce a first product stream comprising acetic acid, water and ethylene and optionally ethane, carbon monoxide and/or carbon dioxide. The acetic acid and ethylene produced in this first reaction zone are then contacted in a second reaction zone with a molecular oxygen-containing gas in the presence of a catalyst to produce a second product stream comprising vinyl acetate, water, acetic acid and optionally ethylene.

It has now been found that the oxidation of a $C_2$ to $C_4$ alkane to produce the corresponding alkene and carboxylic acid, such as the oxidation of ethane to ethylene and acetic acid, and/or the oxidation of a $C_2$ to $C_4$ alkene to produce the corresponding carboxylic acid, such as the oxidation of ethylene to acetic acid can be advantageously operated by maintaining the amount of carbon monoxide in the feed within a defined range.

Accordingly, in a first aspect, the present invention provides a process for the oxidation of a $C_2$ to $C_4$ alkane to produce the corresponding alkene and carboxylic acid and/or for the oxidation of a $C_2$ to $C_4$ alkene to produce the corresponding carboxylic acid, which process comprises feeding to an oxidation reaction zone said alkane and/or alkene, a molecular oxygen-containing gas, carbon monoxide, and optionally water, in the presence of a catalyst active for the oxidation of the alkane to the corresponding alkene and carboxylic acid and/or active for the oxidation of the alkene to the corresponding carboxylic acid, to produce a first product stream comprising alkene and carboxylic acid, characterised in that said carbon monoxide is maintained at between 1% and 20% by volume of the total feed to the oxidation reaction zone.

In a second aspect the present invention relates to an integrated process for the production of an alklenyl carboxylate. Accordingly, the present invention also provides an integrated process for the production of alkenyl carboxylate from a $C_2$ to $C_4$ alkane and/or a $C_2$ to $C_4$ alkene, which process comprises:

(a) feeding to an oxidation reaction zone said alkane and/or alkene, a molecular oxygen-containing gas, carbon monoxide, and optionally water, in the presence of a catalyst active for the oxidation of the alkane to the corresponding alkene and carboxylic acid and/or active for the oxidation of the alkene to the corresponding carboxylic acid, to produce a first product stream comprising alkene and carboxylic acid, and wherein the carbon monoxide is maintained at between 1% and 20% by volume of the total feed to the oxidation reaction zone, and (b) contacting in a second reaction zone at least a portion of said alkene and at least a portion of said carboxylic acid obtained from the oxidation reaction zone, and a molecular oxygen-containing gas, in the presence of at least one catalyst active for the production of alkenyl carboxylate to produce a second product stream comprising alkenyl carboxylate.

In a third aspect the present invention relates to an integrated process for the production of an alkyl carboxylate. Accordingly, the present invention also provides an integrated process for the production of alkyl carboxylate from a $C_2$ to $C_4$ alkane and/or a $C_2$ to $C_4$ alkene, which process comprises:

(a) feeding to an oxidation reaction zone said alkane and/or alkene, a molecular oxygen-containing gas, carbon monoxide, and optionally water, in the presence of a catalyst active for the oxidation of the alkane to the corresponding alkene and carboxylic acid and/or active for the oxidation of the alkene to the corresponding carboxylic acid, to produce a first product stream comprising alkene and carboxylic acid, and wherein the carbon monoxide is maintained at between 1% and 20% by volume of the total feed to the oxidation reaction zone, and (b) contacting in a second reaction zone at least a portion of said alkene, at least a portion of said carboxylic acid obtained from the oxidation reaction zone and, optionally, water, in the presence of at least one catalyst active for the production of alkyl carboxylate to produce a second product stream comprising alkyl carboxylate.

It has now been found that the presence of carbon monoxide (CO) in the feed for the oxidation of $C_2$ to $C_4$ alkanes and/or alkenes suppresses the formation of further carbon monoxide and reduces the overall selectivity to carbon oxides ($CO_x$). In addition, the selectivity to the desired alkene and/or carboxylic acid product or products is increased. For example, using the process of the present invention it has been found that in the oxidation of ethane to ethylene and acetic acid, the selectivity to acetic acid product may be increased. As a further advantage, the reduction in $CO_x$ production (which is a highly exothermic process) allows improved heat control thereby allowing the oxidation reaction to be run at higher productivity.

Preferably the feed comprises a $C_2$ to $C_4$ alkane. The alkane-containing feed may also comprise the corresponding alkene. Where the corresponding alkene is fed with the alkane to the oxidation reaction zone, the oxidation reaction may be operated with a higher amount of alkene in the feed. Conventionally, feeding higher amounts of alkene leads to an increase in $CO_x$ formation. However, with the process of the present invention, the $CO_x$ formation at higher alkene feed amounts (concentrations) is at least partly suppressed by feeding from 1 to 20% by volume of CO. Hence the present invention advantageously allows increased alkene to be fed to the oxidation reaction zone, resulting in enhanced productivity. For example, in the oxidation of ethane and ethylene to acetic acid and ethylene, it has been found that higher amounts of ethylene may be fed to the reactor to give increased productivity.

Preferably, the amount of carbon monoxide in the feed is maintained such that the selectivity to carbon monoxide in the oxidation reaction zone is low, for example, less than 1%. Thus, the amount of carbon monoxide in the first product stream exiting the oxidation reaction zone will not be significantly higher than the amount of carbon monoxide in the feed to the oxidation reaction zone. Carbon monoxide in the first product stream may be separated from the alkene and carboxylic acid components of the first product stream and recycled. Preferably, the carbon monoxide fed to the oxidation reaction zone comprises at least a portion of said recycled carbon monoxide. More preferably essentially all, such as 90% or more, more preferably, 95% or more, of the carbon monoxide in the first product stream may be recycled. Typically, a small amount of carbon monoxide will be formed in the oxidation reaction zone and may be balanced, for example, by losses in the purification stages and/or by a purge stream. Although in theory it is possible to operate with no net carbon monoxide production (zero selectivity to carbon monoxide) in the oxidation reaction zone, in practice a small purge stream will usually be required to prevent build-up of inerts that may be present as impurities in any of the feeds. This preferred carbon monoxide amount (equilibrium amount) will depend on the specific oxidation reaction, the catalyst and the reaction conditions, such as temperature. When operating at this equilibrium amount the process of the present invention has the further advantage that it may be operated without any specific carbon monoxide removal steps (other than any purge), thereby reducing the capital and operating expenditure associated with such steps.

Fresh carbon monoxide may also be fed to the oxidation reaction zone. For example, where it is desirable to operate the oxidation reaction zone such that the carbon monoxide in the feed is consumed to form carbon dioxide at a rate greater than carbon monoxide is produced, fresh CO may be fed to the oxidation reaction zone in addition to recycle CO.

Where the oxidation reaction zone is part of an integrated process, such as that for the production of alkenyl carboxylate, the carbon monoxide fed to the oxidation reaction zone may comprise carbon monoxide recycled from other stages of the integrated process, such as, for example, carbon monoxide recycled, after separation, from the second product stream exiting from the second reaction zone for the production of alkenyl carboxylate.

On start-up, fresh carbon monoxide may be introduced to the feed to the reaction to give the desired amount of carbon monoxide in the total feed. Alternatively, the carbon monoxide amount in the feed to the oxidation reaction zone on start-up may initially be lower than the amount it is desired to maintain, but will build-up to the amount it is desired to maintain in the feed by recycle of the carbon monoxide formed in the process.

Preferably the amount of carbon monoxide in the feed (as fresh and/or recycle component) is maintained at an amount above 2.5% by volume of the total feed, such as above 5% by volume of the total feed, for example above 5 vol % to 20 vol % or above 5 vol % to 15 vol % of the total feed.

Preferably the amount of carbon monoxide in the feed (as fresh and/or recycle component) is maintained at an amount below 15% by volume of the total feed such as in the range above 5 vol % to below 15 vol % of the total feed, for example, above 5 vol % to 10 vol % of the total feed.

Preferably the process for the oxidation of a $C_2$ to $C_4$ alkene to produce the corresponding carboxylic acid is a process for the production of acetic acid from ethylene.

Preferably the process for the oxidation of a $C_2$ to $C_4$ alkane to produce the corresponding alkene and carboxylic acid is a process for the production of ethylene and acetic acid from ethane. Preferably, ethylene is fed to the reaction zone with ethane.

Solid catalysts active for the oxidation of the $C_2$ to $C_4$ alkane and/or alkene may be used in the form of a fixed or fluidised bed. Preferably, the oxidation reaction is performed heterogeneously with solid catalysts and the reactants in the fluid phase Catalysts active for the oxidation of alkane to alkene and carboxylic acid may comprise any suitable catalysts known in the art, for example, for the oxidation of ethane to ethylene and acetic acid as described in U.S. Pat. No. 4,596,787, EP-A-0407091, DE 19620542, WO 99/20592, DE 19630832, WO 98/47850, WO 99/51339, EP-A-0 1043064, WO 9913980, U.S. Pat. Nos. 5,300,682 and 5,300,684, the contents of which are hereby incorporated by reference.

U.S. Pat. No. 4596787 relates to a process for the low temperature oxydehydrogenation of ethane to ethylene using a catalyst having the empirical formula $Mo_aV_bNb_cSb_dX_e$ as therein defined, the elements being present in combination with oxygen.

EP-A-0407091 relates to process and catalyst for the production of ethylene and/or acetic acid by oxidation of ethane and/or ethylene in the presence of an oxidation catalyst comprising molybdenum, rhenium and tungsten.

DE 19620542 relates to molybdenum, palladium, rhenium based oxidation catalysts for the production of acetic acid from ethane and/or ethylene.

WO 99/20592 relates to a method of selectively producing acetic acid from ethane, ethylene or mixtures thereof and oxygen at high temperature in the presence of a catalyst having the formula $Mo_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

WO 98/47850 relates to a process for producing acetic acid from ethane, ethylene or mixtures thereof and a catalyst having the formula $W_aX_bY_cZ_d$ in which X represents one or several of Pd, Pt, Ag and Au, Y represents one or several of V, Nb, Cr, Mn, Fe, Sn, Sb, Cu, Zn, U, Ni, and Bi and Z represents one or several of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and Te, a=1, b>0, c>0 and d is 0 to 2.

WO 99/51339 relates to a catalyst composition for the selective oxidation of ethane and/or ethylene to acetic acid which composition comprises in combination with oxygen the elements $Mo_aW_bAg_cIr_dX_eY_f$ wherein X is the elements Nb and V; Y is one or more elements selected from the group consisting of Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, TI, U, Re and Pd; a,,b, c, d, e and f represent the gram atom ratios of the elements such that $0<a\leqq1$, $0\leqq b<1$ and $a+b=1$; $0<(c+d)\leqq0.1$; $0<e\leqq2$;and $0\leqq f\leqq2$.

EP-A-1043064 relates to a catalyst composition for the oxidation of ethane to ethylene and/or acetic acid and/or for the oxidation of ethylene to acetic acid which composition comprises in combination with oxygen the elements molybdenum, vanadium, niobium and gold in the absence of palladium according to the empirical formula: $Mo_aW_bAu_cV_dNb_eY_f$ wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te and La; a, b, c, d, e and f represent the gram atom ratios of the elements such that: $0<a\leqq1$; $0\leqq b<1$ and $a+b=1$; $10\text{-}5<c\leqq0.02$; $0<d\leqq2$; $0<e\leqq1$; and 0

WO 99/13980 relates to a catalyst for the selective oxidation of ethane to acetic acid of formula: $Mo_aV_bNb_cX_d$ wherein X is at least one promoter element selected from the group consisting of P, B, Hf, Te and As; a is a number ranging from about 1 to about 5; b is 1; c is a number ranging from about 0.01 to about 0.5; and d is a number ranging from greater than 0 to about 0.1.

US 5300682 relates to the use of oxidation catalyst with empirical formula of $VP_aM_bO_x$ where M is one or more of Co, Cu, Re, Fe, Ni, Nb, Cr, W, U, Ta, Ti, Zr, Hf, Mn, Pt Pd, Sn, Sb, Bi, Ce, As, Ag and Au, a is 0.5 to 3, b is 0 1 and x satisfies the valence requirements.

U.S. Pat. No. 5,300,684 relates to a fluid bed oxidation reaction using for example $Mo_{0.37}Re_{0.25}V_{0.26}Nb_{0.07}Sb_{0.03}Ca_{0.02}O_x$.

Other suitable oxidation catalysts for use in the present invention are described in WO 99/13980 which relates to the use of catalysts with elements in combination with oxygen in the relative gram atom ratios of $Mo_aV_bNb_cX_d$ where X=P, B, Hf, Te or As; U.S. Pat. No. 6,030,920 which relates to the use of catalysts with elements in combination with oxygen in the relative gram atom ratios of $Mo_aV_bNb_cPd_d$; WO 00/00284 which relates to the use of catalysts with elements in combination with oxygen in the relative gram atom ratios of $Mo_aV_bNb_cPd_d$ and/or $Mo_aV_bLa_cPd_d$; U.S. Pat. No. 6,087,297 which relates to the use of catalysts with elements in combination with oxygen in the relative gram atom ratios of $Mo_aV_bPd_cLa_d$; WO 00/09260 which relates to the use of catalysts with elements in combination with oxygen in the relative gram atom ratios of $Mo_aV_bLa_cPd_dNb_eX_f$ where X=Cu or Cr and e and f can be zero; WO 00/29106 and WO 00/29105 which relate to the use of catalysts with elements in combination with oxygen in the relative gram atom ratios of $Mo_aV_bGa_cPd_dNb_eX_f$ wherein X=La, Te, Ge, Zn, Si, In or W and WO 00/38833 which relates to the use of catalysts with elements in combination with oxygen in the relative gram atom ratios of $Mo_aV_bLa_cPd_dNb_eX_f$ wherein X=Al, Ga, Ge, or Si, the contents of which are hereby incorporated by reference.

Solid catalysts active for the oxidation of the $C_2$ to $C_4$ alkane and/or alkene may be supported or unsupported. Examples of suitable supports include silica, diatomaceous earth, montmorillonite, alumina, silica alumina, zirconia, titania, silicon carbide, activated carbon and mixtures thereof.

Each of the alkane, molecular oxygen-containing gas, alkene and water may be introduced into the oxidation reaction zone as fresh feed and/or recycle component.

The molecular oxygen-containing gas used in the oxidation reaction zone may be air or a gas richer or poorer in molecular oxygen than air. A suitable gas may be, for example, oxygen diluted with a suitable diluent, for example nitrogen or carbon dioxide. Preferably, the molecular oxygen-containing gas is oxygen. Preferably, at least some of the molecular oxygen-containing gas is fed to the oxidation reaction zone independently from the alkane and optional alkene feeds, and any recycle streams.

The alkane and/or alkene fed into the oxidation reaction zone of the process of the present invention may be substantially pure or may be admixed, for example, with one or more of nitrogen, methane, carbon dioxide, carbon monoxide, hydrogen, and low amounts of $C_3/C_4$ alkenes/alkanes.

Preferably, the total amount of inert impurities, such as methane, nitrogen, carbon dioxide and argon present in the alkene and/or alkane feed is in the range 0 to 3 vol % and more preferably, in the range 0 to 2.5 vol % such as 0 to 2.14 vol %.

Preferably, the total amount of reactive impurities, such as propane and other hydrocarbons, present in the alkene and/or alkane feed is in the range 0 to 10 vol % and more preferably, in the range 0 to 5 vol %.

Fresh carbon monoxide, if used, may be essentially pure or may contain impurities such as carbon dioxide, hydrogen, nitrogen, noble gases and water.

Suitably, the concentration of alkane (as fresh feed and recycle component) is from 0 to 90 mol % inclusive of the total feed, including recycles, to the oxidation reaction zone, preferably from 10 to 80 mol %, more preferably from 40 to 80 mol %.

Suitably, the concentration of alkene (as fresh feed and recycle component) is from 0 to 50 mol % inclusive of the total feed, including recycles, to the oxidation reaction zone, preferably from 1 to 30 mol %, more preferably from 2 to 20 mol %.

Suitably, the concentration of optional water (as fresh feed and recycle component) is from 0 to 50 mol % inclusive of the total feed, including recycles, to the oxidation reaction zone, preferably from 0 to 25 mol %, more preferably from 2 to 15 mol %.

A preferred feed to the oxidation reaction zone for the oxidation of ethane and ethylene to acetic acid and ethylene comprises (in mol %) 40-80% ethane, 2-20% ethylene, 2-15% water, 5-15% carbon monoxide and 5-20% oxygen, with a balance of inert gases, such as argon, carbon dioxide and/or nitrogen. The oxygen is preferably added directly in to the fluidized bed.

When solid catalysts are used in the oxidation reaction zone alkane and/or alkene, molecular-oxygen containing gas and any recycle gases are preferably passed through the oxidation reaction zone with a residence time corresponding to a combined gas hourly space velocity (GHSV) of 500-10,000 $hr^{-1}$; the GHSV being defined as volume (calculated at STP) of gas passing through the reactor divided by the bulk volume of settled catalyst.

The oxidation reaction of the present invention may suitably be carried out at a temperature in the range from 100 to 400° C., typically in the range 200 to 380° C., preferably 250 to 350° C.

The oxidation reaction of the present invention may suitably be carried out at atmospheric or superatmospheric pressure, for example in the range from 80 to 400 psig.

Typically, alkane conversions in the range 1 to 99% may be achieved in the oxidation reaction of the present invention.

Typically, oxygen conversions in the range 30 to 100% may be achieved in the oxidation reaction of the present invention.

In the oxidation reaction of the present invention, the catalyst suitably has a productivity in the range 10 to 10000 grams of carboxylic acid, such as acetic acid, per hour per kilogram of catalyst.

The first product stream from the oxidation process may be fed directly to a downstream process, but preferably is fed to a downstream process indirectly after one or more separation stages, such as removal of carbon monoxide by separation or reaction. Hence, in the second aspect of the present invention, at least a portion of the alkene and at least a portion of the carboxylic acid obtained from the oxidation reaction zone are contacted with molecular oxygen-containing gas to produce alkenyl carboxylate, such as vinyl acetate. In the third aspect of the present invention, at least a portion of the alkene and at least a portion of the carboxylic acid obtained from the oxidation reaction zone are contacted with a suitable catalyst to produce alkyl carboxylate, such as ethyl acetate. Preferably, alkane is oxidized in the presence of a suitable oxidation catalyst in the first oxidation reaction zone to produce an approximately 1:1 ratio of alkene and carboxylic acid for use in the subsequent alkenyl carboxylate or alkyl carboxylate reaction. However alkene or carboxylic acid may be added to (or removed from) the first product stream as required to give the desired feed to the second reaction zone. Hence, optional additional alkene and/or optional additional carboxylic acid may be added, or carboxylic acid and/or alkene may be recovered from the first product stream prior to the second reaction zone.

The additional alkene may be fresh alkene and/or recycled alkene from the second reaction zone.

Additional alkene introduced into the second reaction zone for the production of alkenyl carboxylate or alkyl carboxylate may be substantially pure or may be admixed, for example, with one or more of nitrogen, argon, methane, carbon dioxide, carbon monoxide, hydrogen, and low amounts of $C_3/C_4$ alkenes/alkanes.

Advantageously, in the second aspect of the present invention, high concentrations of alkene are fed to the second reaction zone and low concentrations of alkene are fed to the oxidation reaction zone. Low concentrations (less than 20 mol % of total feed) of alkene fed to the oxidation reaction zone allow the required equimolar or approximate equimolar mixture of alkene and carboxylic acid to be produced. High concentrations of alkene (greater than 50 mol % of the total feed) fed to the second reaction zone maximize the selectivity to alkenyl carboxylate product such as vinyl acetate.

Desirably, the concentration of alkene, such as ethylene, fed to the second reaction zone in the second aspect of the invention is at least 50 mol % of the total feed to the second reaction zone, preferably, at least 55 mol %, more preferably at least 60 mol %. Suitably, the concentration of alkene is up to 85 mol % of the total feed to the second reaction zone, preferably, in the range at least 50 mol % to 80 mol %, such as at least 55 mol % to 80 mol %.

Advantageously, in the third aspect of the present invention optimal concentrations of alkene are fed to the second reaction zone and low concentrations of alkene are fed to the oxidation reaction zone. Low concentrations (less than 20 mol % of total feed) of alkene fed to the oxidation reaction zone allow the required equimolar or approximate equimolar mixture of alkene and carboxylic acid to be produced. Optimal concentrations of alkene may be fed to the second reaction zone to maximize the selectivity to alkyl carboxylate product, such as ethyl acetate.

Desirably, the concentration of alkene, such as ethylene, fed to the second reaction zone is at least 50 mol % of the total feed to the second reaction zone, preferably, at least 55 mol %, more preferably at least 60 mol %.

Catalysts known in the art for the production of alkenyl carboxylates may be used in the second aspect of the process of the present invention. Thus, catalyst active for the production of vinyl acetate which may be used in a second reaction zone of the present invention may comprise, for example, catalysts as described in GB 1 559 540; U.S. Pat. No. 5,185,308 and EP-A-0672453 the contents of which are hereby incorporated by reference.

GB 1 559 540 describes a catalyst active for the preparation of vinyl acetate by the reaction of ethylene, acetic acid and oxygen, the catalyst consisting essentially of: (1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per litre of catalyst, and the gold being present in an amount of from 0.5 to 2.25 grams per litre of catalyst, and (3) from 5 to 60 grams per litre of catalyst of alkali metal acetate. U.S. Pat. No. 5,185,308 describes a shell impregnated catalyst active for the production of vinyl acetate from ethylene, acetic acid and an oxygen containing gas, the catalyst consisting essentially of: (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

EP-A-0672453 describes palladium containing catalysts and their preparation for fluid bed vinyl acetate processes.

Catalysts known in the art for the production of alkyl carboxylates may be used in the third aspect of the process of the present invention. Catalysts active for the production of alkyl carboxylates which may be used in the second reaction zone may comprise, for example, catalysts as described in EP-A-0926126; the contents of which are hereby incorporated by reference.

EP-A-0926126 describes a process for the production of esters by reacting, in a plurality of reactors set up in series, ethylene, propylene or mixtures thereof with a saturated aliphatic $C_1$-$C_4$ mono-carboxylic acid in the presence of a heteropolyacid catalyst.

Typically, the production of alkenyl carboxylate, such as vinyl acetate, or alkyl carboxylate, such as ethyl acetate, in the second reaction zone is carried out heterogeneously with the reactants being present in the gas phase.

The molecular oxygen-containing gas used in the second reaction zone for the production of alkenyl carboxylate may comprise unreacted molecular oxygen-containing gas from the oxidation reaction zone and/or additional molecular oxygen-containing gas.

The additional molecular oxygen-containing gas, if used, may be air or a gas richer or poorer in molecular oxygen than air. A suitable additional molecular oxygen-containing gas may be, for example, oxygen diluted with a suitable diluent, for example nitrogen, argon or carbon dioxide. Preferably, the additional molecular oxygen-containing gas is oxygen. Preferably, at least some of the molecular oxygen-containing gas is fed independently to the second reaction zone from the alkene and carboxylic acid reactants.

In the third aspect of the present invention water may optionally be added in the second reaction zone for the production of alkyl carboxylate. When present, the water is suitably present in the form of steam and in an amount in the range 1-10 mol % of the total feed to the second reaction zone.

The additional carboxylic acid fed to the second reaction zone for the production of alkenyl carboxylate or alkyl carboxylate may comprise fresh acid and/or recycle acid. Preferably, at least a portion of the carboxylic acid introduced in to the second reaction zone comprises carboxylic acid produced from the oxidation reaction zone.

The fresh and recycle carboxylic acid may be introduced into the second reaction zone either as separate feed streams or as a single feed stream comprising both fresh and recycle acid.

The recycle carboxylic acid fed to the second reaction zone for the production of alkenyl carboxylate or alkyl carboxylate may comprise at least a portion of the acid obtained from downstream processes such as from the separation of unreacted acid from the second product stream.

At least part of the carboxylic acid fed to the second reaction zone may be liquid. When solid catalysts are used in the second reaction zone for the production of alkenyl carboxylate, the alkene, the carboxylic acid, any additional alkene or carboxylic acid reactants, any recycle streams and molecular oxygen-containing gas are preferably passed through the second reaction zone at a combined gas hourly space velocity (GHSV) of 500-10,000 $hr^{-1}$.

The second reaction zone for the production of alkenyl carboxylate may suitably be operated at a temperature in the range from 140 to 200° C.

The second reaction zone for the production of alkenyl carboxylate may suitably be operated at a pressure in the range 50 to 300 psig.

The second reaction zone for the production of alkenyl carboxylate may suitably be operated as either a fixed or a fluidised bed process.

Carboxylic acid conversions in the range 5 to 80% may be achieved in the second reaction zone for the production of alkenyl carboxylate.

Oxygen conversions in the range 20 to 100% may be achieved in the second reaction zone for the production of alkenyl carboxylate.

Alkene conversions in the range 3 to 100% may be achieved in the second reaction zone for the production of alkenyl carboxylate.

Suitably, the selectivity based on the alkene to the alkenyl carboxylate product, such as vinyl acetate of at least 85%, such as at least 90% may be achieved in the second reaction zone In the second reaction zone for the production of alkenyl carboxylate, the catalyst suitably has a productivity in the range 10 to 10000 grams of alkenyl carboxylate per hour per kg of catalyst.

When ethane is used in the process of the second aspect of the present invention, the product stream from the second reaction zone for the production of alkenyl carboxylate may comprise vinyl acetate, water and acetic acid and optionally also unreacted ethylene, ethane, oxygen, acetaldehyde, nitrogen, argon, carbon monoxide and carbon dioxide. Such a product stream may be separated by azeotropic distillation into an overhead fraction comprising vinyl acetate and water and a base fraction comprising acetic acid and water. The base fraction is removed from the distillation column as liquid from the bottom of the column. Additionally, a vapour from one or more stages above the bottom of the column may also be removed. Prior to such a distillation step, ethylene, ethane, acetaldehyde, carbon monoxide and carbon dioxide, if any, may be removed from the second product stream, suitably as an overhead gaseous fraction from a scrubbing column, in which a liquid fraction comprising vinyl acetate, water and acetic acid is removed from the base. The carbon monoxide, if any, may be recycled to the oxidation reaction zone. The ethylene and/or ethane may be recycled to the oxidation reaction zone and/or the second reaction zone.

Vinyl acetate is recovered from the overhead fraction, suitably for example by decantation. The recovered vinyl acetate may, if desired, be further purified in known manner.

The base fraction comprising acetic acid and water may be recycled, with or preferably without further purification, to the second reaction zone. Alternatively, acetic acid is recovered from the base fraction and may be further purified if desired, in known manner, for example, by distillation.

Where ethane is used in the process of the second aspect of the present invention, preferably the acetic acid and ethylene are separated from the effluent, including carbon monoxide, from the oxidation reaction zone (ethane oxidation reactor) prior to reaction of the acetic acid and ethylene in the second reaction zone (VAM reactor). The remaining effluent may be treated as desired, for example to remove at least some of the $CO_2$ produced, and recycled to the oxidation reaction zone to maintain the carbon monoxide amount in the feed to said reaction zone. The process of the present invention obviates the need for or mitigates the scale required for any carbon monoxide removal process steps (for example, as required in the process disclosed in WO 01/90042).

In another embodiment of the second aspect of the present invention at least some of the carbon monoxide in the effluent from the oxidation reaction zone may be fed to the second reaction zone to maintain a suitable carbon monoxide amount in the feed to the second reaction zone. Carbon monoxide, including any further carbon monoxide that may be produced in the second reaction zone, may be subsequently separated from second product stream and recycled to the oxidation reaction zone to maintain the required carbon monoxide amount in the feed to the oxidation reaction zone.

BRIEF DESCRIPTION OF THE DRAWINGS

The process of the present invention will now be illustrated with respect to the figures and examples.

With reference to FIG. 1, a feedstream (1), comprising fresh ethane and oxygen, and optional water and ethylene, and a recycle stream (2) comprising unreacted ethane and carbon monoxide are fed to a fluid bed ethane oxidation reactor having a bed of suitable oxidation catalyst (3) for the production of acetic acid and ethylene. The feed has 1 to 20% by volume of carbon monoxide. The oxidation reaction produces a product stream (4) comprising acetic acid, ethane, ethylene, carbon monoxide, carbon dioxide, water and any inert gas that is present in the feed and/or recycle streams. The water and acetic acid are separated in a suitable first separation means (5), for example in a scrubber, to provide a gaseous stream (6) comprising predominantly ethane, ethylene, carbon monoxide and carbon dioxide. Optionally, water may be removed from the acetic acid using a suitable separation means, such as distillation. At least some of the carbon dioxide from gaseous stream (6) may be removed in a $CO_2$ removal system (7), for example, using potassium carbonate. At least some of any inert gas present and some of the ethylene from stream (6) may be recovered by separation in a suitable second separation means (8), to leave a stream (2) comprising unreacted ethane, carbon monoxide and any remaining inerts, $CO_2$ or ethylene, which is recycled to the ethane oxidation reactor (3), to maintain the required carbon monoxide amount. A purge may be taken from this recycle stream, or elsewhere, to prevent build-up of inerts.

FIG. 2 is generally similar to FIG. 1 and thus the same reference numerals are used, where appropriate. In FIG. 2, the recovered acetic acid and water stream from the first separation means (5) and the recovered ethylene stream from the second separation means (8), together with oxygen, and optional additional acetic acid and/or ethylene as necessary are then fed to a vinyl acetate reactor (9), wherein they are contacted with a suitable catalyst to give a second product stream comprising vinyl acetate. Optionally, prior to the feeding the acetic acid and water stream from the first separation means to the vinyl acetate reactor (9), at least a portion of said acetic acid and water stream may be fed to a suitable separation means to remove at least a portion of the water therein, for example, in a distillation column. Any carbon monoxide in the second product stream may be separated and combined with recycle stream (2) for recycle to the fluid bed ethane oxidation reactor (3). Any unreacted ethylene and acetic acid, in the second product stream may be separated and recycled to the vinyl acetate reactor (9).

EXAMPLES

Figure 1:
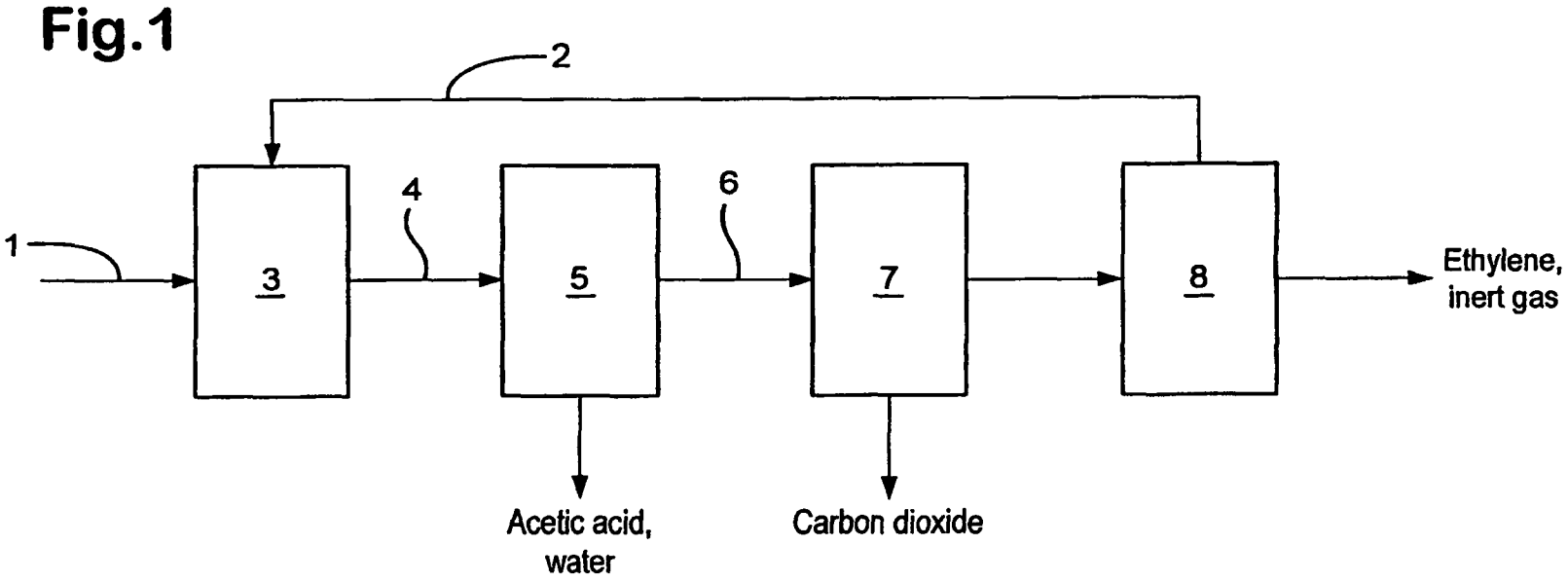
FIG. 1 represents, in schematic form, a process for the oxidation of ethane and ethylene to acetic acid and ethylene.
Figure 2:
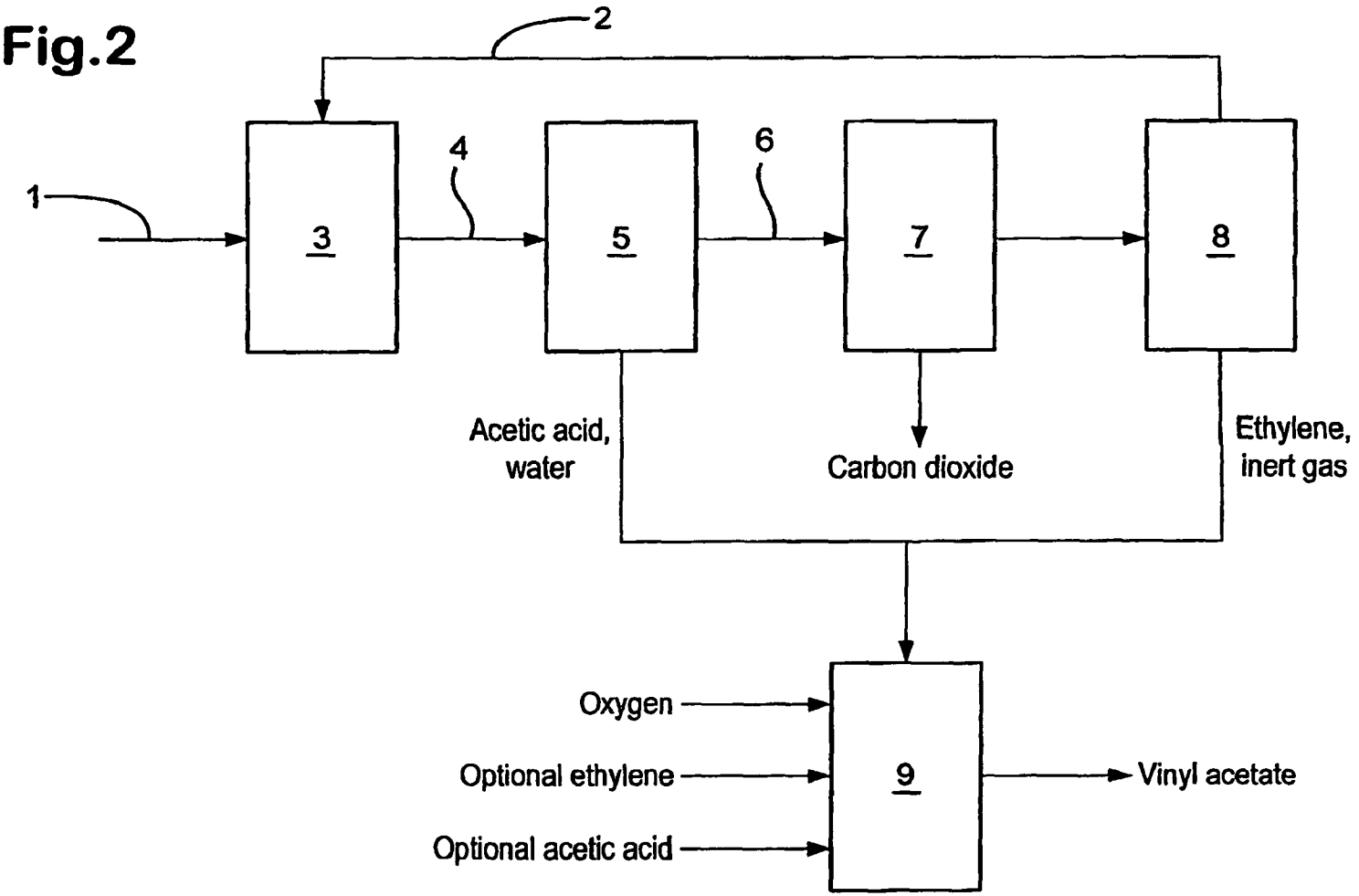
FIG. 2, represents, in schematic form, an integrated process for the production of vinyl acetate from ethane and ethylene according to the second aspect of the present invention.

Carbon monoxide at various amounts was added to a feed to a reactor for the oxidation of ethane to acetic acid. The feed comprised 60 vol % ethane, 5 vol % ethylene, 5 vol % water, 6 vol % oxygen, the requisite amount of carbon monoxide, with a balance of nitrogen. The feed was passed over an ethane oxidation catalyst at temperatures of approximately 302° C., 293° C. and 283° C. respectively. The results are given in Table 1 below.

TABLE 1

| CO in feed | Conversion (%) | Selectivity (C-mol %) | | | | |
|---|---|---|---|---|---|---|
| (mole %) | Oxygen | Ethylene | CO | $CO_2$ | COx | AcOH |
| 302° C., 16 barg, 3200/h, 60% ethane, 5% ethylene, 5% water, 6.6% oxygen, balance nitrogen. | | | | | | |
| 0 | 98.0 | 55.9 | 9.9 | 3.8 | 13.7 | 30.4 |
| 2.5 | 96.8 | 52.4 | 8.7 | 4.4 | 13.1 | 34.5 |
| 5 | 97.4 | 51.2 | 5.0 | 6.1 | 11.1 | 37.6 |
| 10 | 96.9 | 52.8 | 0.7 | 7.7 | 8.4 | 38.8 |
| 293° C., 16 barg, 3200/h, 60% ethane, 5% ethylene, 5% water, 6.6% oxygen, balance nitrogen. | | | | | | |
| 0 | 82.6 | 55.3 | 9.8 | 3.8 | 13.6 | 31.2 |
| 2.5 | 79.5 | 51.6 | 8.3 | 4.2 | 12.5 | 35.8 |
| 5 | 82.8 | 50.3 | 4.9 | 6.1 | 11.0 | 38.7 |
| 10 | 81.5 | 54.2 | −1.3 | 8.3 | 7.1 | 38.8 |
| 283° C., 16 barg, 3200/h, 60% ethane, 5% ethylene, 5% water, 6.6% oxygen, balance nitrogen. | | | | | | |
| 0 | 64.5 | 50.7 | 10.4 | 4.1 | 14.5 | 34.8 |
| 2.5 | 60.1 | 53.1 | 8.7 | 4.1 | 12.8 | 34.1 |
| 5 | 63.8 | 47.7 | 5.0 | 6.2 | 11.2 | 41.1 |
| 10 | 61.4 | 51.8 | −2.9 | 8.1 | 5.2 | 43.0 |

These results show that on increasing the amount of CO in the feed to the reactor the amount of CO formed is suppressed. The suppression of CO is not compensated by an equivalent increase in the $CO_2$ formation, resulting in a net decrease in total carbon oxides ($CO_x$) formation and an increase in acetic acid selectivity.

These results also demonstrate that the point at which CO formation is totally inhibited (no net CO production) is dependent on the temperature of the oxidation reaction zone. Thus, at a higher temperature a higher concentration of carbon monoxide in the feed to the oxidation reaction zone is required to completely inhibit CO formation.

The invention claimed is:

1. A process for the oxidation of a $C_2$to $C_4$ alkane to produce the corresponding alkene and carboxylic acid and/or for the oxidation of a $C_2$ to $C_4$ alkene to produce the corresponding carboxylic acid, which process comprises feeding to an oxidation reaction zone said alkane and/or alkene, a molecular oxygen-containing gas, carbon monoxide, and optionally water, in the presence of a catalyst active for the oxidation of the alkane to the corresponding alkene and carboxylic acid and/or active for the oxidation of the alkene to the corresponding carboxylic acid, to produce a first product stream comprising alkene and carboxylic acid, characterised in that said carbon monoxide is maintained at between 1% and 20% by volume of the total feed to the oxidation reaction zone, *wherein the $C_2$-$C_4$ alkane is ethane, the $C_2$ to $C_4$ alkene is ethylene and the carboxylic acid is acetic acid.*

2. A process according to claim 1 which further comprises contacting in a second reaction zone at least a portion of said alkene and at least a portion of said carboxylic acid obtained from the oxidation reaction zone, and a molecular oxygen-containing gas, in the presence of at least one catalyst active for the production of alkenyl carboxylate to produce a second product stream comprising alkenyl carboxylate, *wherein the alkenyl carboxylate is vinyl acetate.*

3. A process according to claim 1 which further comprises contacting in a second reaction zone at least a portion of said alkene, at least a portion of said carboxylic acid obtained from the oxidation reaction zone and, optionally, water, in the presence of at least one catalyst active for the production of alkyl carboxylate to produce a second product stream comprising alkyl carboxylate, *wherein the alkyl carboxylate is ethyl acetate*.

4. A process according to claim 1 wherein the carbon monoxide is fed to the oxidation reaction zone as a fresh gas and/or as a recycle gas.

5. A process according to claim 1 wherein the first product stream comprises carbon monoxide.

6. A process according to claim 5 wherein at least 90% of the carbon monoxide present in the first product stream is recycled to the oxidation reaction zone.

7. A process according to claim 2 wherein the second product stream comprises carbon monoxide.

8. A process according to claim 7 wherein carbon monoxide is separated from the second product stream and recycled to the oxidation reaction zone.

9. A process according to claim 1 wherein the amount of carbon monoxide in the feed (as fresh and/or recycle gas) is maintained above 2.5% by volume of the total feed.

10. A process according to claim 9 wherein the amount of carbon monoxide is maintained above 5% by volume of the total feed.

11. A process according to claim 9 wherein the amount of carbon monoxide is maintained in the range above 5% by volume to 20% by volume of the total feed.

12. A process according to claim 9 wherein the amount of carbon monoxide is maintained in the range above 5% by volume to 15% by volume of the total feed.

13. A process according to claim 1 wherein the amount of carbon monoxide in the feed (as fresh and/or recycle gas) is maintained below 15% by volume of the total feed.

14. A process according to claim 13 wherein the amount of carbon monoxide is maintained in the range above 5% by volume to below 15% by volume of the total feed.

15. A process according to claim 13 wherein the amount of carbon monoxide is maintained in the range above 5% by volume to 10% by volume of the total feed.

[16. A process according to claim 1 wherein the $C_2$-$C_4$ alkane is ethane, the $C_2$ to $C_4$alkene is ethylene and the carboxylic acid is acetic acid.]

17. A process according to claim 1 wherein ethane and ethylene are fed to the oxidation reaction zone.

18. A process according to claim 1 wherein each of the alkane and alkene is fed to the oxidation reaction zone as fresh feed and/or as a recycle component.

19. A process according to claim 1 wherein the concentration of alkane (as fresh feed and recycle component) is from 0 to 90 mol % of the total feed to the oxidation reaction zone.

20. A process according to claim 1 wherein the concentration of alkene (as fresh feed and recycle component) is from 0 to 50 mol % of the total feed to the oxidation reaction zone.

21. A process according to claim 1 in which water is fed to the oxidation zone as fresh feed and/or recycle component in a concentration in the range greater than 0 to 50 mol % of the total feed.

22. A process according to claim 1 wherein the [mel] *mol* ratio of alkene to carboxylic acid in the first product stream is approximately 1:1.

[23. A process according to claim 2 wherein the alkenyl carboxylate is vinyl acetate.]

24. A process according to claim 2 wherein additional alkene and/or additional carboxylic acid is fed to the second reaction zone.

25. A process according to *claim 2* wherein the concentration of alkene fed to the oxidation reaction zone is less than 20 mol % of the total feed and/or the concentration of alkene fed to the second reaction zone is greater than 50 mol % of the total feed.

26. A process according to claim 2 wherein the concentration of alkene fed to the second reaction zone is at least 60 mol % of the total feed.

27. A process according to claim 25 or claim 26 wherein the alkene is ethylene.

28. A process according to claim 2 wherein the second reaction zone is a fixed bed or a fluidised bed reactor.

[29. A process according to claim 3 wherein the alkyl carboxylate is ethyl acetate.]

30. A process according to claim 3 or claim 29 wherein water is fed to the second reaction zone in an amount in the range 1 to 10 mol % of the total feed.

31. A process according to claim 1 wherein the oxidation reaction is carried out at a temperature in the range 100 to 400° C.

32. A process according to claim 1 wherein the total amount of inert impurities present in the alkene and/or alkane feed to the oxidation reactor is in the range 0 to 3 vol %.

33. A process according to claim 1 wherein the total amount of reactive impurities present in the alkene and/or alkane feed to the oxidation reactor is in the range 0 to 10 vol %.

* * * * *